United States Patent
Squires et al.

(10) Patent No.: US 7,342,597 B2
(45) Date of Patent: Mar. 11, 2008

(54) RADIO FREQUENCY IDENTIFICATION TAGS ON CONSUMABLE ITEMS USED IN PRINTERS AND RELATED EQUIPMENT

(75) Inventors: Milo B. Squires, Chaska, MN (US); Roger D. McCumber, Minnetonka, MN (US); Jeffrey A. Davie, Ham Lake, MN (US); Arthur Paulson, Minneapolis, MN (US); Bill Myntti, Elk River, MN (US); Luc G. Debleeckere, Plymouth, MN (US)

(73) Assignee: DataCard Corporation, Minnetonka, MN (US)

( * ) Notice: Subject to any disclaimer, the term of this patent is extended or adjusted under 35 U.S.C. 154(b) by 79 days.

(21) Appl. No.: 11/146,611

(22) Filed: Jun. 7, 2005

(65) Prior Publication Data

US 2005/0275708 A1 Dec. 15, 2005

Related U.S. Application Data

(63) Continuation of application No. 10/308,244, filed on Dec. 2, 2002, now Pat. No. 6,963,351.

(60) Provisional application No. 60/342,781, filed on Dec. 21, 2001, provisional application No. 60/400,331, filed on Jul. 31, 2002.

(51) Int. Cl.
*B41J 32/00* (2006.01)
(52) U.S. Cl. .................................... 347/214
(58) Field of Classification Search ........ 347/171–172, 347/193, 214, 217–218, 188; 400/207–208, 400/214, 196, 611–613, 120.01, 120.02, 76, 400/615.2; 428/36.9
See application file for complete search history.

(56) References Cited

U.S. PATENT DOCUMENTS 4,797,018 A 1/1989 Hofmann et al.

(Continued)

FOREIGN PATENT DOCUMENTS

EP 0 903 237 A2 3/1999

(Continued)

OTHER PUBLICATIONS

United States District Court for the District of Minnesota, Reply to Counterclaims of DataCard Corporation and NBS Technologies, Inc. and Card Technology Corporation's Counterclaim for Declaratory Judgement, Court File No. 05-cv-02546 (MJD/SRN), Filed Mar. 2, 2006, pp. 1-11.

(Continued)

*Primary Examiner*—K. Feggins
(74) *Attorney, Agent, or Firm*—Hamre, Schumann, Mueller & Larson, P.C.

(57) ABSTRACT

Improvements relating to identification tags on consumable supply items used in identity document production equipment. The use of identification tags on the consumable supply items allows the document production equipment to recognize the consumable supply items that are loaded into each piece of equipment. The equipment can then initiate a variety of activities that are based on the loaded supply item. The activities are designed to enhance the operation of the equipment for the equipment operator and to provide added value to those customers who utilize consumable supply items that are recognized by the equipment.

20 Claims, 5 Drawing Sheets

U.S. PATENT DOCUMENTS

| | | | |
|---|---|---|---|
| 4,806,958 | A | 2/1989 | Momot et al. |
| 4,880,325 | A | 11/1989 | Ueda et al. |
| 5,003,333 | A | 3/1991 | Earnhart |
| 5,035,325 | A | 7/1991 | Kitsuki |
| 5,079,565 | A | 1/1992 | Shimizu et al. |
| 5,138,344 | A | 8/1992 | Ujita |
| 5,184,152 | A | 2/1993 | French |
| 5,266,968 | A | 11/1993 | Stephenson |
| 5,305,020 | A | 4/1994 | Gibbons et al. |
| 5,318,370 | A | 6/1994 | Nehowig |
| 5,385,416 | A | 1/1995 | Maekawa et al. |
| 5,389,992 | A | 2/1995 | Weber |
| 5,398,257 | A | 3/1995 | Groenteman |
| 5,455,617 | A | 10/1995 | Stephenson et al. |
| 5,755,519 | A | 5/1998 | Klinefelter |
| 5,774,639 | A | 6/1998 | Schildkraut et al. |
| 5,809,358 | A | 9/1998 | Weber |
| 5,829,897 | A * | 11/1998 | Murai .................... 400/615.2 |
| 5,949,335 | A | 9/1999 | Maynard |
| 6,014,088 | A | 1/2000 | Van Santbrink et al. |
| 6,022,207 | A | 2/2000 | Dahlin et al. |
| 6,047,579 | A | 4/2000 | Schmitz |
| 6,059,469 | A | 5/2000 | Hirumi |
| 6,099,178 | A | 8/2000 | Spurr et al. |
| 6,106,166 | A | 8/2000 | Spurr et al. |
| 6,227,643 | B1 | 5/2001 | Purcell et al. |
| 6,247,857 | B1 | 6/2001 | Wheeler et al. |
| 6,249,226 | B1 | 6/2001 | Harrison et al. |
| 6,386,772 | B1 | 5/2002 | Klinefelter et al. |
| 6,573,923 | B2 | 6/2003 | Hevenor et al. |
| 2002/0059880 | A1 | 5/2002 | Klinefelter et al. |
| 2003/0059050 | A1 | 3/2003 | Hohberger et al. |
| 2003/0186009 | A1 * | 10/2003 | Odamura et al. .......... 428/36.9 |
| 2006/0191022 | A1 | 8/2006 | Hohberger et al. |

FOREIGN PATENT DOCUMENTS

| | | |
|---|---|---|
| EP | 0 903 237 A3 | 3/1999 |
| EP | 0 979 736 A1 | 2/2000 |
| EP | 1 066 975 A1 | 1/2001 |
| JP | 1-224980 | 9/1989 |
| JP | 1-310987 | 12/1989 |
| WO | WO 90/00974 | 2/1990 |
| WO | WO 00/43932 | 7/2000 |

OTHER PUBLICATIONS

Hohberger, et al., U.S. Appl. No. 60/314,926: "Method and Apparatus for Article Authentication", filed Aug. 24, 2001; pp. 1 and 21-22 of the description, and pp. 11-12 and 15-17 of the drawings from the electronic file wrapper on PAIR.

A document prepared by Applicant titled Information on Pending Litigation; 1 page.

United States District Court for the Northern District of Illinois, Complaint for Declaratory Relief by Zebra Technologies Corporation and Zebra Technologies International, LLC v. DataCard Corporation, Civil Action No. 1:06-cv-04159; filed Aug. 2, 2006; 6 pages.

United States District Court for the Northern District of Illinois, Zebra Technologies Corporation and Zebra Technologies International, LLC v. DataCard Corporation, Civil Action No. 1:06-cv-04159, Notice of Voluntary Dismissal With Prejudice; Nov. 9, 2006; 2 pages.

United States District Court for the District of Minnesota; Card Technology Corporation's Answers To Defendant DataCard Corporation's Interrogatories; Court File No. 05-cv-02546 (MJD/SRN); Dated Jun. 12, 2006; pp. 1, 31, 33 and 38.

United States District Court for the District of Minnesota; Card Technology Corporation v. DataCard; Order of Partial Dismissal With Prejudice; Court File No. 05-cv-02546 (MJD/SRN); Dated Nov. 9, 2006; 1 page.

"Temic Semiconductors TK5550," *Telefunken Semiconductors*, 2 pages (Apr. 30, 1997).

"Temic Semiconductors e5550," *Telefunken Semiconductors*, 11 pages (Mar. 17, 1998).

"Zebra (Eltron) Card Printers - news, Card Printer Solutions, The World's Most Popular Card Printers," *Zebra Technologies Corporation, Eltron Card Printer Division*, 2 pages (Oct. 31, 2002).

"Zebra *i* Series, Frequently Asked Questions," *Zebra Technologies Card Imaging* Division, 5 pages (Oct. 2003, ©2002 ZIH Corp.).

Exhibit 1, "Hand Sketches of RFID tags known by Applicants for Fargo Electronics and Eltron/Zebra," 1 page (made on Aug. 20, 2004).

* cited by examiner

RADIO FREQUENCY IDENTIFICATION TAGS ON CONSUMABLE ITEMS USED IN PRINTERS AND RELATED EQUIPMENT

PRIORITY DATA

This application is a Continuation application of application Ser. No. 10/308,244 filed Dec. 2, 2002, now U.S. Pat. No. 6,963,351, which application is incorporated by reference herein in its entirety, and which claims the benefit of U.S. Provisional Application No. 60/342,781 filed Dec. 21, 2001, and U.S. Provisional Application No. 60/400,331 filed Jul. 31, 2002.

FIELD OF THE INVENTION

This invention relates to consumable items in printers and related equipment. More particularly, the invention relates to a system for tagging consumable supply items that are used in equipment, such as printers, used to produce data bearing identity documents, including cards such as identification cards, drivers licenses, credit cards and the like, and booklets such as passports and the like, as well as to methods resulting from the use of tagged consumables.

BACKGROUND OF THE INVENTION

The use of radio frequency (RF) identification tags on consumable supply items of printers is known in the art. U.S. Pat. Nos. 5,455,617; 6,099,178; 6,227,643; and WO 00/43932 are examples. Each of these documents disclose the use of read/write memory fixed onto a consumable item of a printer, and from which data is read and/or written to by a radio frequency circuit.

There is, however, a continuing need for improvements relating to the use of memory tags on consumable items that are used in the production of data bearing identity documents.

SUMMARY OF THE INVENTION

The invention provides improvements relating to the use of identification tags on consumable supply items used in identity document production equipment. The use of identification tags on the consumable supply items allows the document production equipment to recognize the consumable supply items that are loaded into each piece of equipment. The equipment can then initiate a variety of activities that are based on the loaded supply item. The activities are designed to enhance the operation of the equipment for the equipment operator and to provide added value to those customers who utilize consumable supply items that are recognized by the equipment.

In one aspect of the invention, a consumable supply item for a piece of data bearing document production equipment is provided. The supply item comprises a core, a ribbon material wound onto the core, and a memory element attached to the core.

In another aspect of the invention, a printer is provided which comprises a ribbon material supply roll disposed on a spindle, a read/write memory element fixed to the supply roll, and a read/write unit for reading data from and writing data to the read/write memory element.

In yet another aspect of the invention, a method of operating a piece of data bearing document production equipment is provided. The method includes loading a consumable supply item containing a memory element having stored data into the piece of equipment, using the piece of equipment to read data from the memory element, determining whether the loaded consumable supply item is a recognized supply item based upon the data that is read from the memory element, and initiating an activity in the piece of equipment that is different from a normal operating activity of the piece of equipment when the loaded consumable supply item is a recognized supply item.

In another aspect of the invention, the read/write memory element is fixed to the take-up core upon which used print ribbon is wound, instead of being fixed to the supply core. In this embodiment, it is also preferred that ribbon amount data stored in the memory element pertaining to how much ribbon remains on the supply roll, is decremented based on print jobs performed by the printer. Print job information is available from the printer controller which controls operation of the printer in which the take-up core is used.

For a better understanding of the invention, its advantages and objects obtained by its use, reference should be made to the drawings which form a further part hereof, and to the accompanying description, in which there is described a preferred embodiment of the invention.

DETAILED DESCRIPTION OF THE INVENTION

The invention relates to the use of memory tags on consumables items, preferably consumable items provided in the form of rolls, that are used in the production of data bearing identity documents, including cards such as identification cards, drivers licenses, credit cards and the like, and booklets such as passports and the like. Examples of consumable items to which the invention applies includes, but is not limited to, printing ribbons, cleaning tape, indent foil, labels, topping foil, holographic topcoats, polyester laminates, ink cartridges for ink jet printers, and toner cartridges. The printing ribbons can have multi-color panels, or they can be a single color. The types of equipment that utilize these consumables includes printers and laminators, as well as peripheral equipment utilized with printers and laminators. In addition, the memory tags of the invention can be used on equipment that form part of large scale document production units, or on table top units.

The invention includes a memory element that is provided on the consumable item so that data pertaining to the consumable item, and other data, can be stored thereon. The memory element is preferably a read/write memory element that allows data to be read from and written to the memory element. In addition, a suitable read/write unit is provided that interacts with the memory element in order to read data from, and write data to, the memory element.

In order to describe the inventive concept, the invention will be described herein in relation to a print ribbon roll on a printer that is used in the production of data bearing identity documents. It is to be understood, however, that the invention is applicable to other types of consumables in other types of identity document production equipment as well.

Figure 1:
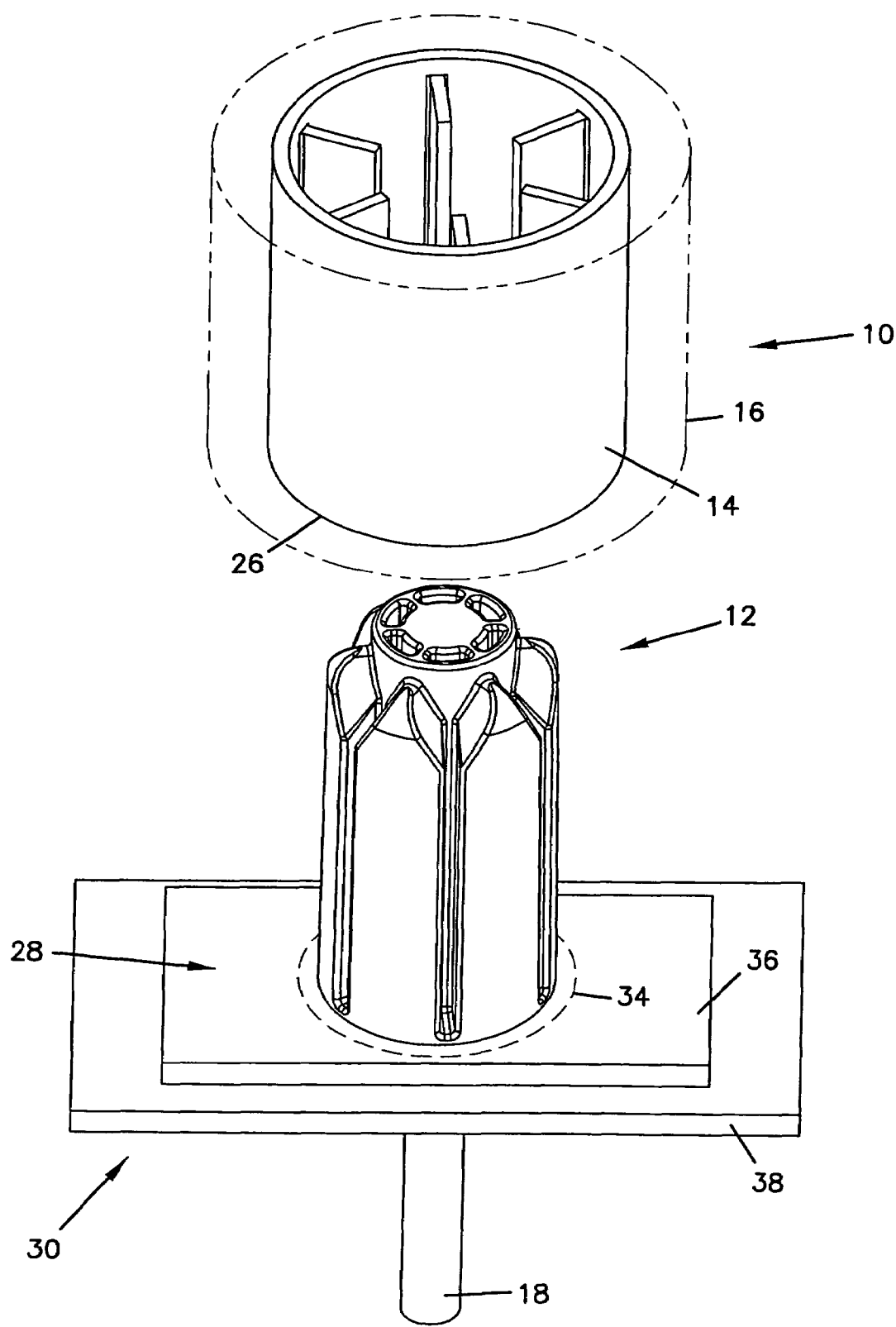
FIG. 1 illustrates a print ribbon supply roll and spindle arrangement for a printer incorporating the radio frequency identification tag according to the present invention.

FIG. 1 illustrates a print ribbon supply roll 10 and a spindle 12 for use in a printer. The ribbon supply roll 10 includes a ribbon core 14 and a print ribbon 16 wound onto the core 14. The print ribbon 16, which is illustrated in dashed lines in FIG. 1, preferably comprises a series of differently colored panels, such as cyan, yellow, magenta, and black. Alternatively, the print ribbon 16 comprises a single, solid color, i.e. monochromatic. The spindle 12 is mounted so as to be rotatably driven by a shaft 18 via a motor, such as a stepper motor (not shown), in known fashion. The ribbon core 14 and ribbon 16 are designed to be placed onto the spindle 12 whereby the ribbon core 14 is driven by the spindle 12 to unwind ribbon 16 therefrom during use of the printer. The ribbon 16 is taken up on a take-up core (FIG. 5) within the printer.

Figure 2:
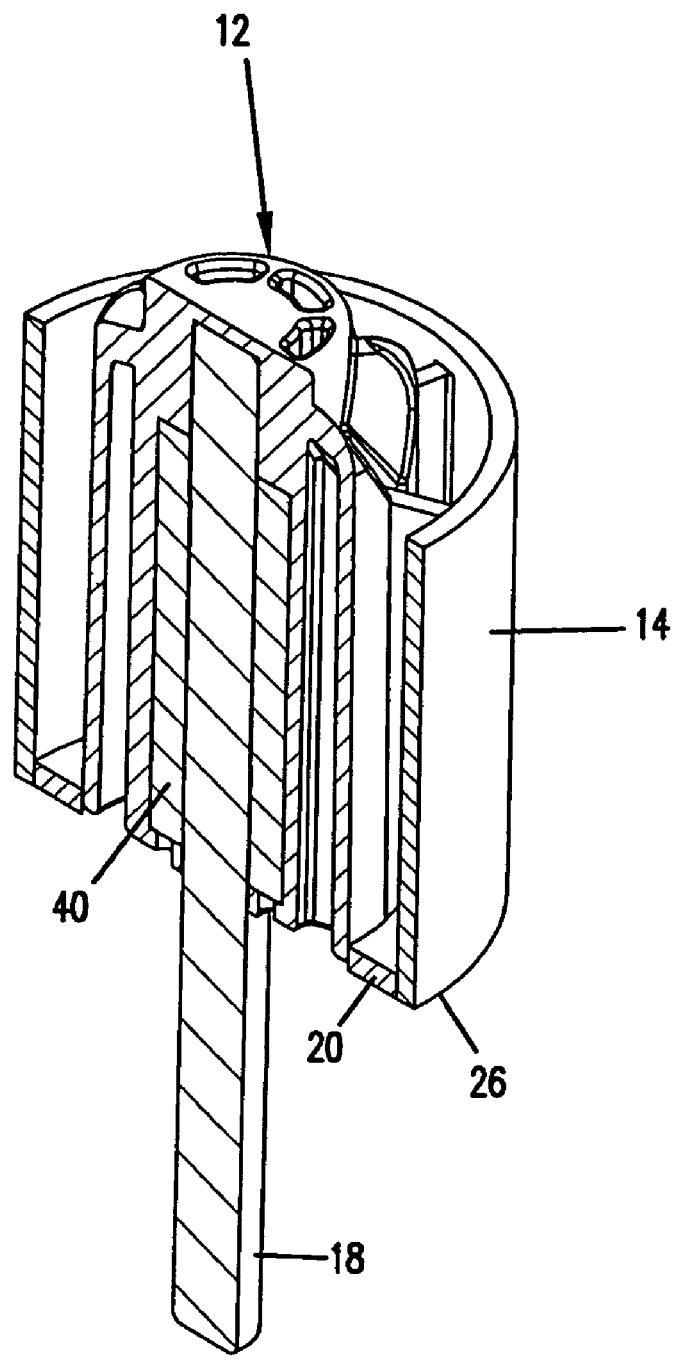
FIG. 2 is a cross sectional view of the core and spindle arrangement.
Figure 3:
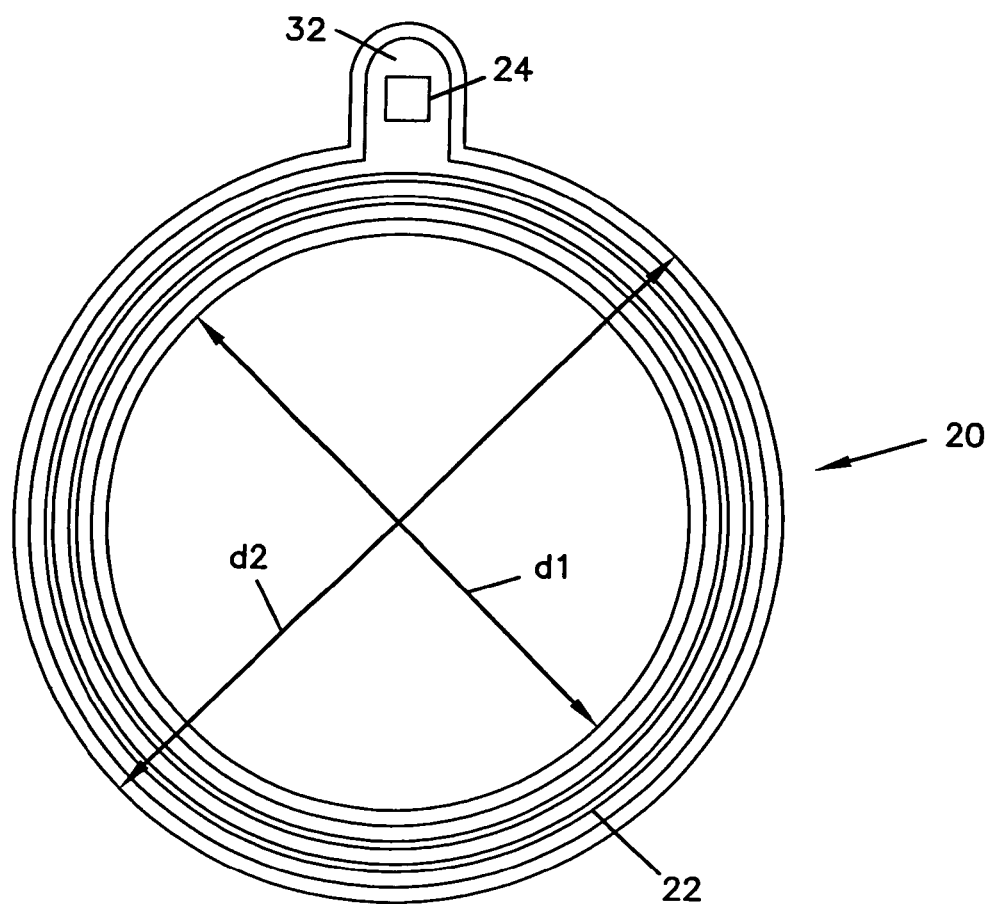
FIG. 3 is a top view of the radio frequency identification tag of the present invention.

Affixed to the core 14 is an identification tag 20 (see FIGS. 2 and 3). The tag 20 comprises an antenna 22 and a read/write memory element 24. In the preferred embodiment, the tag 20 is fixed to an end 26 of the core 14. In addition, a radio frequency read/write unit 28 is positioned on structure 30 adjacent the end 26 of the core 14 for reading data from, writing data to, and providing power to, the tag 20. The present invention utilizes radio frequency signals to read data from and write data to the memory element 24, as well as to provide power for the tag 20. The use of radio frequency signals to read and write data, and to provide power to identification tags, is well known in the art, such as from WO 00/43932 and U.S. Pat. No. 6,099,178. As the use of radio frequency identification tags is known, a description of how data is read from and written to the tags, and how the tags are powered by the radio frequency signals, is not provided herein.

The identification tag 20, details of which are shown in FIG. 3, is generally circular, and is designed to fit within the end 26 of the core 14. The core 14 is slightly recessed adjacent the end 26 to allow the tag 20 to fit completely within the interior of the core 14. The tag 20 is preferably fastened to the core 14, for example by using an adhesive material. Therefore, the tag 20 is fixed to the core 14 to prevent its easy removal. Other fastening mechanisms could be used to secure the tag 20 to the core 14, such as a snap fastening system in which the tag 20 snaps into place on the core 14. If desired, the tag 20 could be mounted to the core 14 so as to allow non-destructive removal of the tag 20. The inner diameter $d_1$ of the tag 20 is slightly greater than the outer diameter of the spindle 12 to allow the tag 20 to slide over the spindle 12 as the core 14 is introduced onto the spindle 12. The outer diameter $d_2$ of the tag 20 is slightly less than the interior diameter of the core 14 to allow the tag 20 to fit within the recessed end 26 of the core 14. The antenna 22 is circular and is formed on the tag 20 between the inner and outer diameters. A tab 32 projects from the outer edge of the tag 20, and the memory element 24 is disposed on the tab 32. In use, the tab 32 is preferably bent upward toward the middle of the core 14 when the tag 20 is mounted within the core 14. The tab 32 could also be bent downward toward the open end of the core 14, in which the size of the tab 32 must be selected so that the end of the tab does not project beyond the end of the core 14.

Returning now to FIG. 1, the read/write unit 28 includes an antenna 34 that is housed within a plastic cover 36 forming part of the structure 30. The antenna 34 is generally circular, and has a diameter that is greater than the spindle 12. Other known components of the read/write unit 28 that cooperate with the antenna 34 for reading and writing data to the tag 20 are also housed within the plastic cover 36.

The structure 30 also includes a metal plate 38. The metal plate 38 can be steel or aluminum, and have any thickness. However, to provide optimum performance, it has been discovered that the metal plate 38 must cover a diameter of at least about 2.375 inches around the shaft 18. By using a metal plate 38 of at least this size, it has been discovered that the inductance of the antenna can be made constant which results in the radio frequency signals being made constant, thereby improving the performance. The diameter of the shaft 18 should also be no more than 0.375 inches in diameter. It is to be realized that both the plastic cover 36 and the metal plate 38 are provided with apertures to allow passage of the shaft 18. Bearings permit rotation of the shaft 18 relative to the plastic cover 36 and metal plate 38.

The spindle 12 is preferably molded from a plastic material. As illustrated in FIG. 2, a ferrite core 40 is molded inside the spindle 12 during formation of the spindle, and the core 40 and spindle 12 are molded around the shaft 18. At present, RF identification tag technology is such that the tag 20 should be as close as possible to the read/write unit to provide optimal performance. Normally, the core 14 is disposed on the spindle 12 so that the tag 20 is disposed at the bottom of the core 14 adjacent the antenna 34 of the read/write unit 28. However, if the core 14 is reversed and is placed on the spindle 12 so that the tag 20 is at the top of the core 14, the tag 20 is further away from the antenna 34. The ferrite core 40 that is molded in the spindle helps direct the lines of flux of the RF signal to the top of the core 14. Therefore, if the tag 20 is disposed at the top end of the core 14, the RF signals from the read/write unit 28 are still effectively transmitted to the top end of the core and the tag 20, to allow effective reading and writing of data. This also reduces interference with other tags that may be adjacent the tag 20. For topping foil, which is normally mounted in a horizontal orientation, the tag would generally be provided at one end only.

An important aspect of the RF identification tag system of the present invention is the data that is stored on the memory element 24, and how that data is utilized. It is preferred that the data identify the type of supply material that is present on the core 14. In addition, the data should include a unique identifier that identifies the specific roll. Preferably, reading of the data on the tag 20 is automatically performed every time a ribbon is loaded into the printer, as well as each time the printer is re-started.

Figure 4:
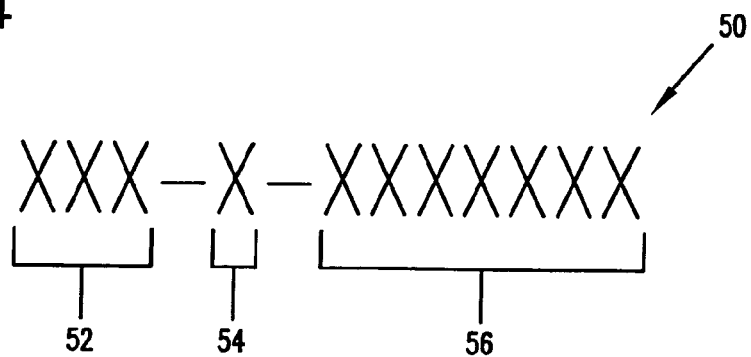
FIG. 4 illustrates an identification code that can be stored on the memory element.

FIG. 4 illustrates an exemplary identification code 50 that is stored in the memory element 24. The code 50 is preferably an eleven digit numeric ID code. However, it is contemplated that the code 50 could be formed from alphabetic characters, alphanumeric characters, symbolic characters, and combinations thereof.

The first three digits of the code 50 represent a particular supply item identifier number 52. The use of three digits allows up to 999 supply items to be identified. For example, one type of print-ribbon roll from a particular manufacturer could be assigned the identifier number 123, while a second, different type of print ribbon roll from the same manufacturer could be assigned the identifier number 423. A look-up table within the equipment's operating system stores information, such as by supply item identifier number, for each supply item supported by the equipment. By reading the supply item identifier number 52, information pertaining to the supply item can thus be accessed. The supply item identifier number 52 could be formed by a larger or smaller number of digits, depending upon the number of supply items that need to be identified.

The code 50 also includes a date identifier portion 54 which identifies the year the supply item was produced. The last digit of the year in which the supply item was produced is preferably used. For example, if the supply item was produced in the year 2001, the digit used in the date identifier 54 would be "1". The date identifier 54 could utilize a larger number of digits to represent the year if desired. It is also contemplated that the code 50 could be used without the date identifier 54.

The last portion of the code 50 is an individual supply item identification number 56 that is unique to the individual supply item. The use of seven digits allows up to 9,999,999 individual supply item ID numbers to be used. The identification number 56 allows the equipment's operating system to store information for each individual supply item, so that each individual supply item can be tracked and monitored. The supply item identification number 56 could be represented by a larger or smaller number of digits, depending upon how many individual supply items are to be tracked and monitored.

In addition to the identification code 50, additional data that can be stored on the memory element 24 of the tag 20 includes, but is not limited to:

1) Data indicating how much useable ribbon remains on the roll, i.e. ribbon amount data. This data can be continuously updated in known fashion during equipment use by tracking ribbon use and decrementing the ribbon amount data based upon use. An alternative, as discussed below, is to decrement the ribbon amount data based upon-print jobs, with this information being provided by the printer controller.
2) Data pertaining to the offsets to be applied to the equipment based upon the particular ribbon; i.e. system offset data.
3) Data pertaining to the use history of the ribbon, i.e. use history data. The data can include information relating to the type(s) of equipment (if any) the roll has been previously used in; the times and/or dates of previous uses and roll loading/unloading events, both in previous equipment and in the equipment the roll is presently loaded in; the operator(s) of the equipment; how many data bearing identity documents have been produced using the roll, for each use and/or total; and information as to whether any problems with the roll or the equipment occurred during roll use.
4) Manufacturer data.
5) Promotional/Marketing data.

Some of this data can be stored in a look-up table(s) in the system memory of the equipment, rather than being stored in the memory element 24, with the data being accessed by reading the supply item identifier number 52 and/or the individual supply item identification number 56 from the code 50. This would minimize the storage requirements of the memory element 24. However, in some instances it is preferred to store as much of this data as possible on the memory element, which would allow the ribbon roll to be used in equipment that do not have, or have access to, look-up tables containing the needed data.

As a result of the tag 20, the operation of the equipment with which the supply item is used can be enhanced based upon the particular supply item that is loaded into the equipment. A specific implementation of this concept will be described in relation to the use of print ribbon rolls in a printer. When a print ribbon roll that is loaded into the-printer is determined by the operating system of the printer to be from a first pre-determined group of print ribbon rolls, as determined by reading the supply item identifier number 52 from the code 50 or by a failure to read any data, e.g. the print ribbon roll does not have a tag, the printer operates in its usual fashion which will be referred to hereinafter as the printer's "normal mode". However, when a print ribbon roll loaded into the printer is determined by the operating system of the printer to be from a second pre-determined group of print ribbon rolls, as determined by reading the supply item identifier number 52 from the code 50, the operation of the printer can be enhanced via the printer's operating system initiates various system activities that are based on the loaded print ribbon roll. This enhanced operation will be referred to hereinafter as the printer's "enhanced mode". The supply item identifier number(s) belonging to the first and second predetermined groups can be stored in look-up tables in the printer's operating system. A print ribbon roll without a tag will default to the printer normal mode operation.

Numerous enhancements can be realized in the printer enhanced mode. These enhancements include enhanced printer operation, data tracking and reporting, error proofing, and inventory management.

Printer Operation

In current print ribbon rolls without an RF ID tag, in order to determine the type of print ribbon on the roll, it is necessary for the operator to manually identify the ribbon type to the printer by entering the ribbon type using a printer user interface unit. This process is time consuming and inconvenient for the operator. It also requires a printer operator with sufficient skill to enter the ribbon type. Alternatively, it is known to automatically identify a print ribbon by advancing the print ribbon a certain distance to enable the printer to determine the print ribbon type. Because the print ribbon is advanced for identification purposes, this process wastes ribbon that could have been used for printing.

Because of the tag 20, the printer knows the type of ribbon on the roll by reading the code 50. Therefore, the printer can automatically optimize its operation based upon the loaded ribbon type. Further, ribbon useage is reduced since the ribbon is not advanced for identification purposes. This minimum advancement feature is applicable in the printer normal mode, for those rolls belonging to the first predetermined group. As an added benefit in the enhanced mode for those rolls determined to be in the second pre-determined group, ribbon useage can be maximized by backing-up the ribbon so that previously used portions of the ribbon are re-used.

Further, for those rolls determined to be in the second pre-determined group, printer servicing operations can be optimized. For example, when the printer shuts down as a result of a sensed problem, and the operator completes all validation checks resulting from the shut down, the printer can be set-up to automatically resume operation without requiring the operator to send the printer an acknowledgement, provided the loaded roll is determined to be from the second pre-determined group. For a loaded roll determined to be from the first pre-determined group, the printer would require that an acknowledgement from the operator be input, prior to resuming operation. In addition, for impending servicing needs, such as a low print ribbon, the printer can be set-up to provide an indicator to the operator of the impending servicing need, and indicate to the operator the location of the servicing need.

An additional benefit provided to the second pre-determined group is that the printer can be set-up to display an icon that provides a graphical display of the amount of ribbon remaining on the roll. For example, the icon can be a thermometer bar, an odometer, or the like. Text can accompany the icon to indicate the percent of ribbon remaining. In addition, the icon can be colored to match the color of the ribbon. In contrast, for the first pre-determined group, the printer can be set-up to simply provide an indication as to whether the print ribbon is loaded or not.

Data Tracking and Reporting

For a roll determined to be from the second pre-determined group, the printer can be set-up to perform a variety of data tracking, data analyzing, and data reporting functions. For example, when a print ribbon is loaded, data from the memory element or from a look-up table, such as the offsets required by the ribbon, can be read and applied to the printer, and data, such as the time and date, can be written to the memory element or look-up table.

During use of the ribbon, data, such as the number of documents produced and operating time to allow determination of throughput rate, can be stored in the memory element or a look-up table. The throughput rate can then be displayed and/or analyzed.

Similarly, when the ribbon roll is unloaded from the printer, data pertaining to the unloaded ribbon is stored in the memory element or in a look-up table.

Error Proofing

For a roll determined to be from the second pre-determined group, certain error proofing features will result. For example, the printer is set-up to perform a check of the ribbon to determine ribbon compatibility with the printer by checking a material compatibility look-up table stored in the printer operating system. The printer determines whether there are any compatibility issues and displays recommendations to the operator. The operator can also be given a choice whether to proceed or not. Further, if the ribbon type is improper (e.g. cleaning tape is loaded instead of a print ribbon), a warning message and/or indicator can be displayed.

In addition, the printer is preferably set-up to automatically apply the system offset data for ribbons from the second pre-determined group. For ribbons from the first pre-determined group, the offset information for a particular ribbon must be manually entered by the operator after being prompted for the offset information.

For the second pre-determined group, the printer is also set-up to verify that the loaded print ribbon is suitable for the current document production job. If it is not, a warning message will be provided and the printer will pause until the error has been corrected. Once corrected, the printer will automatically resume operation.

Also for the second pre-determined group, the printer will detect if the loaded roll is from a re-called lot (determined from the code 50), and provide a warning message on a suitable display as well as instructions on how to deal with the issue. The instructions can be updated as needed by updating the re-call information stored in the printer's operating system.

Inventory Management

A further enhancement is that data reports can be generated for the printer detailing information on the ribbons that have been loaded into the printer per time period. This enhancement is available for the second pre-determined group. In addition, the printer preferably tracks and counts each time a roll from the second pre-determined group is loaded into the printer. In more advanced applications, the printer can track the detailed useage of a ribbon roll from the second pre-determined group, as well as generate reports detailing the ribbons that have been consumed over a pre-determined time period.

In each of the enhancements described herein, it is contemplated that the operating system of the printer can access and communicate with a remote or host controller via a modem, a network, or other suitable communication technology. The look-up tables and other data storage capacity necessary to implement the enhancements can thus be provided by the remote controller, rather than locally at the printer.

Figure 5:
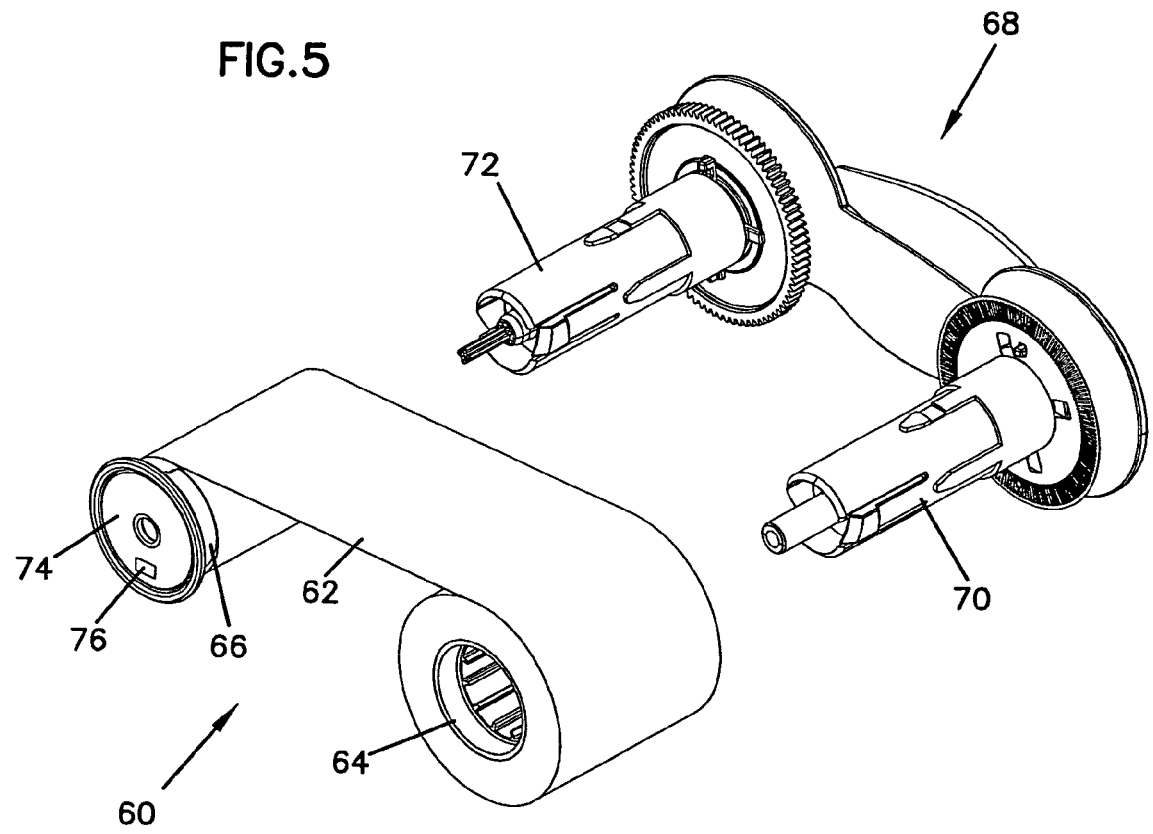
FIG. 5 illustrates an alternate embodiment of the invention utilizing a memory element on the take-up core.

The tag has so far been described as being attached to a ribbon supply core. However, other tag locations are possible. FIG. 5 illustrates a print ribbon supply item 60 that includes a print ribbon 62, preferably a multi-color print ribbon, that supplies the dye or ink used in the printing process. The ribbon 62 is wound onto a supply core or cylinder 64 that is cylindrical in shape. The ribbon 62 includes a take-up end that is attached to a take-up core or cylinder 66 that is cylindrical in shape and upon which used ribbon is wound. In FIG. 5, the ribbon 62 is illustrated as being unused, with substantially the entire extent thereof wound onto the supply cylinder 64, and the end of the ribbon 62 being attached to the take-up cylinder 66 ready to take-up used ribbon.

The supply item 60 is intended to be mounted on a carrier 68 that includes a rotatable supply spindle 70 that receives the supply cylinder 64 thereon and a rotatable take-up spindle 72 that receives the take-up cylinder 66 thereon. A cap 74 is attached to the end of the take-up cylinder 66, and fixed to the cap 74 in a suitable manner is an RF identification tag 76. In this embodiment, a suitable RF read/write unit for reading data from and to the tag 76 will be positioned adjacent the end of the take-up cylinder 66.

Figure 6:
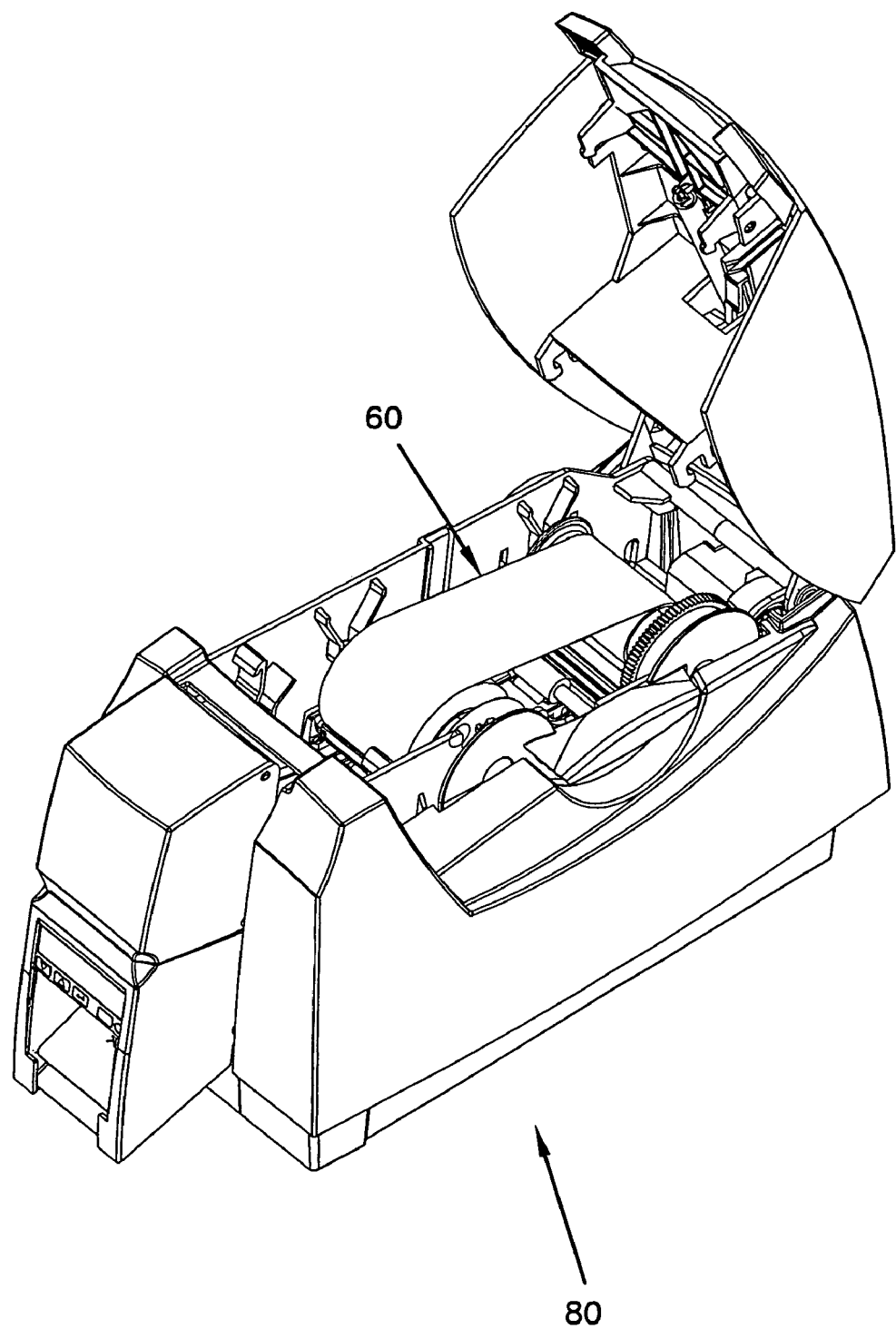
FIG. 6 illustrates a printer in which the ribbon supply and ribbon take-up of FIG. 5 can be used.

FIG. 6 illustrates the supply item 60 positioned within a desktop thermal printer 80. The printer 80 is related to the printer disclosed in U.S. Pat. No. 5,762,431, the entire disclosure of which is incorporated by reference. The printer 80 is used to print data and/or graphics onto plastic cards, for example financial (e.g. credit and debit) cards, drivers' licenses, national identification cards, and other cards. The printer 80 can also be provided with features to perform additional processing operations on the cards, including laminating the cards, printing bar codes, reading from and/or writing to magnetic stripes on the cards, and reading from and/or writing to an integrated circuit chip on the card. After positioning the supply item 60 on the carrier 68, the carrier 68 is then inserted into the printer 80 which positions the print ribbon 62 for subsequent printing.

The tag 76 can store data that is the same as, or different from, the data stored in the tag 20. Preferably, the tag 76 permits the printer 80 to operate with the same enhancements as described above.

It is preferred that the tag 76 store at least data concerning the amount of ribbon remaining on the supply cylinder 64. This data is preferably decremented during use of the printer, so that the tag 76 contains information on how much ribbon remains. Preferably, the ribbon remaining data on the tag 76 is decremented based upon the print jobs performed by the printer 80 using information provided by the printer controller.

For most print jobs, the printer controller can determine approximately how much ribbon will be needed to complete each print job. Therefore, the ribbon remaining data can be decremented by the amount of ribbon expected to be used for each print job. An excess margin, if needed, can be factored into the expected ribbon use determination to account for discrepancies and errors. Thus, as each print job is completed, or sometime thereafter, the ribbon remaining data on the tag 76 is updated by the information provided by the printer controller.

Other ways for determining the amount of ribbon used can be used. For example, an encoder could be used in association with the supply cylinder 64 or on the supply side of the supply item 60 to directly track ribbon use. Alternatively, an encoder could ride on the surface of the ribbon on the supply cylinder to rotate in proportion to the amount of ribbon that gets unspooled from the supply cylinder 64. A capstan encoder or other encoder device downstream from the supply cylinder 64 and in engagement with the print ribbon could also be used to directly track ribbon use.

In one implementation, the tag 76 also preferably stores an encryption string to make the tag 76 difficult to reproduce. The tag 76 can also store one or more of the following: a part number, information on the ribbon type, a date code, a manufacturers lot code, a manufacturers code, and copyright information. The tag 76 can also store a count that is decremented, for example after each print job, to enable the tag 76 to expire once the count reaches zero or other chosen value.

In addition, the tag could be positioned to hang off the end of the supply or take-up cylinders and not rotate with the cylinder during use. In such an embodiment, the tag would be fixed in position relative to the cylinder during printer operation, such as by the tag cooperating with a slot in the printer upon inserting the carrier into the printer. The tag could also be separate from the supply and take-up cylinders, and instead be placed by a user into the printer when the supply item is replaced.

The above specification, examples and date provide a complete description of the invention. Many embodiments of the invention, not explicitly described herein, can be made without departing from the spirit and scope of the invention.

What is claimed is:

1. A consumable supply for equipment having a rotatable spindle, comprising:
    a cylinder having first and second open ends and a spindle passageway extending along a rotation axis between the first and second open ends to enable the cylinder to be disposed on the rotatable spindle of the equipment;
    a consumable web material connected to the cylinder;
    a electronic tag body attached to the cylinder adjacent the first or second open end, the tag body having an aperture formed therethrough configured to allow passage through the tag body of at least a portion of the spindle or a portion of an element connected to the spindle when the cylinder is disposed on the spindle, and the aperture being aligned with the rotation axis, the tag body further comprising a circular antenna surrounding the aperture, an outer diameter of the antenna being greater than an outer dimension of the aperture and less than an outer diameter of the cylinder.

2. The consumable supply of claim 1, wherein the electronic tag body further comprises a programmable read/write memory element.

3. The consumable supply of claim 1, wherein the aperture is generally circular.

4. The consumable supply of claim 3, wherein the consumable supply is configured for use in a printer or a laminator.

5. The consumable supply of claim 1, wherein the cylinder is a supply cylinder supplying consumable web material for use by the equipment.

6. The consumable supply of claim 1, wherein the cylinder is a take-up cylinder that takes-up consumable web material that has been used by the equipment.

7. The consumable supply of claim 1, wherein the consumable web material comprises print ribbon, cleaning tape, indent foil, labels, topping foil, holographic topcoats, or polyester laminates.

8. The consumable supply of claim 1, wherein the an inner diameter of the antenna is larger than an outer dimension of the aperture.

9. The consumable supply of claim 1, wherein the aperture is sized so that the spindle is rotatable relative to the tag body.

10. The consumable supply of claim 1, wherein the web material is a color print ribbon with a series of colored panels including cyan, yellow and magenta panels.

11. The consumable supply of claim 1, wherein the tag body is non-destructively attached to the cylinder to allow non-destructive removal of the tag body.

12. An electronic identification tag for use on a consumable supply item in equipment having a rotatable spindle, the supply item having a cylinder configured to be disposed on the rotatable spindle of the equipment for rotating the cylinder, comprising:
    a portable tag body non-destructively removably connectable to the cylinder, the tag body having an aperture formed therethrough configured to allow passage through the tag body of at least a portion of the spindle or a portion of an element connected to the spindle when the tag body is attached to the cylinder and the cylinder is disposed on the spindle; the tag body comprising a memory, and a circular antenna surrounding the aperture, an outer diameter of the antenna is greater than an outer dimension of the aperture and less than an outer diameter of the cylinder.

13. The electronic identification tag of claim 12, wherein the memory is read/write memory.

14. The electronic identification tag of claim 12, wherein the aperture is sized so that the spindle is rotatable relative to the tag body.

15. The radio frequency identification tag of claim 12, wherein the aperture is generally circular.

16. The electronic identification tag of claim 12 wherein the memory comprises data to enable enhanced operation of the consumable supply item in the equipment.

17. A printer ribbon supply for use in a card printer having a rotatable spindle, comprising:
    a core having first and second ends and a spindle passageway extending along a rotation axis between the first and second ends to enable the core to be disposed on the rotatable spindle of the card printer;
    a print ribbon connected to the core, the print ribbon including a series of colored panels including cyan, yellow, and magenta panels;
    a radio frequency identification tag non-destructively connected to the core adjacent the first or second end thereof to allow non-destructive removal of the tag, the tag having an aperture formed therethrough that is configured to allow passage through the tag of at least a portion of the spindle when the core is disposed on the spindle, and the aperture being aligned with the rotation axis;

the tag having a circular antenna that is concentric with the rotation axis; and the tag having a memory element.

18. The printer ribbon supply of claim 17, wherein the panels include black panels.

19. The printer ribbon supply of claim 17, wherein the core has an interior diameter, and the tag has an outer diameter that is less than the interior diameter.

20. The printer ribbon supply of claim 19, wherein the tag is recessed into the first end or the second end of the core.

* * * * *